US012797631B2

(12) United States Patent
Huang

(10) Patent No.: US 12,797,631 B2
(45) Date of Patent: Nov. 17, 2026

(54) INTELLIGENT PHOTO-BIOLOGICAL TREATMENT DEVICE FOR EYES AND EYE TRAINING METHOD

(71) Applicant: SHENZHEN CHUYING SHIJIE HEALTH TECHNOLOGY CO., LTD., Shenzhen (CN)

(72) Inventor: Xiaoqiu Huang, Shenzhen (CN)

(73) Assignee: SHENZHEN CHUYING SHIJIE HEALTH TECHNOLOGY CO., LTD., Shenzhen (CN)

( * ) Notice: Subject to any disclaimer, the term of this patent is extended or adjusted under 35 U.S.C. 154(b) by 698 days.

(21) Appl. No.: 18/270,502

(22) PCT Filed: Apr. 11, 2023

(86) PCT No.: PCT/CN2023/087682

§ 371 (c)(1),
(2) Date: Jun. 30, 2023

(87) PCT Pub. No.: WO2023/226607

PCT Pub. Date: Nov. 30, 2023

(65) Prior Publication Data

US 2024/0374914 A1 Nov. 14, 2024

(30) Foreign Application Priority Data

May 24, 2022 (CN) ......................... 202210575934.2

(51) Int. Cl.
*A61N 5/06* (2006.01)
*A61M 21/00* (2006.01)

(52) U.S. Cl.
CPC ........... *A61N 5/0613* (2013.01); *A61M 21/00* (2013.01); *A61M 2021/0027* (2013.01);
(Continued)

(58) Field of Classification Search
CPC .......... A61N 5/0613; A61N 2005/0648; A61N 2005/0659; A61N 2005/0647;
(Continued)

(56) References Cited

U.S. PATENT DOCUMENTS 8,945,197 B1 2/2015 Friend et al.
2006/0106276 A1* 5/2006 Shealy .................. A61M 21/00 600/27
(Continued)

FOREIGN PATENT DOCUMENTS

CN 203010505 U * 6/2013
CN 204420712 U 6/2015
(Continued)

*Primary Examiner* — Jennifer Robertson
*Assistant Examiner* — Brogan R Landeen

(57) ABSTRACT

Disclosed is an intelligent photo-biological treatment device for eyes and eye training method. The device includes a device body including a first cover and a second cover; a side of each of the first and second covers facing a human eye has a first cavity and a second cavity; the first cavity has an infrared emission module; the second cavity has a photo-biological training room; an assembly groove of a rubber-iron element of the infrared emission module has a reflective film, a light guide plate, a diffusive film, a lower brightness enhancement film, an upper brightness enhancement film, and a black-black double-sided tape; an infrared light-emitting diode (LED) point light source is located at one side of the light guide plate; the infrared LED point light source is configured to emit infrared light; and the device body has a controller electrically connected with the infrared LED point light source.

9 Claims, 4 Drawing Sheets

(52) U.S. Cl.
CPC .................. *A61N 2005/063* (2013.01); *A61N 2005/0648* (2013.01); *A61N 2005/0651* (2013.01); *A61N 2005/0659* (2013.01); *A61N 2005/0666* (2013.01)

(58) Field of Classification Search
CPC .... A61N 2005/0626; A61N 2005/0615; A61N 2005/0666; A61N 2005/0662; A61N 2005/0663; A61M 21/00; A61M 21/02; A61M 2205/50; A61M 2205/052; A61M 2021/0044; G02B 6/0053; G02B 6/0055; G02B 6/0051

USPC ......... 600/27; 604/20; 607/88, 100, 54, 112, 607/141; 349/62, 57, 13; 362/612, 620

See application file for complete search history.

(56) References Cited

U.S. PATENT DOCUMENTS

| | | | | |
|---|---|---|---|---|
| 2016/0067087 | A1* | 3/2016 | Tedford | A61N 5/0624 606/4 |
| 2020/0289321 | A1* | 9/2020 | Luo | A61B 5/4812 |

FOREIGN PATENT DOCUMENTS

| | | | | | |
|---|---|---|---|---|---|
| CN | 204798346 | U | | 11/2015 | |
| CN | 207396915 | U | * | 5/2018 | |
| CN | 208670634 | U | | 3/2019 | |
| CN | 106773237 | B | * | 2/2020 | G02F 1/133504 |
| CN | 211132071 | U | * | 7/2020 | |
| CN | 112137849 | A | | 12/2020 | |
| CN | 114870275 | A | | 8/2022 | |
| JP | 2006270073 | A | * | 10/2006 | |
| JP | 2011146238 | A | * | 7/2011 | |
| KR | 20150056025 | A | * | 5/2015 | H10W 90/00 |
| WO | WO-2018201618 | A1 | * | 11/2018 | G02F 1/133617 |

* cited by examiner

INTELLIGENT PHOTO-BIOLOGICAL TREATMENT DEVICE FOR EYES AND EYE TRAINING METHOD

TECHNICAL FIELD

The present disclosure belongs to the technical field of vision health, and in particular relates to an intelligent photo-biological treatment device for eyes and eye training method.

BACKGROUND

In recent years, due to work and lifestyle habits, our eyes have to work for an increasingly long time. In order to alleviate eye fatigue, eye massage machines emerged on the market. The existing eye massage machines perform mechanized or heated massages around the eyes to relax eye muscles and enhance their blood circulation. However, the existing eye massage machines can only temporarily alleviate eye fatigue, but cannot fundamentally improve vision health.

SUMMARY

An objective of the present disclosure is to provide an intelligent photo-biological treatment device for eyes and eye training method, in order to solve most if not all of the technical problems existing in the prior art.

To achieve the above objective, the present disclosure adopts the following technical solutions:

A first aspect of the present disclosure provides an intelligent photo-biological treatment device for eyes. The intelligent photo-biological treatment device for eyes includes a device body, where the device body includes a first cover and a second cover that are respectively adapted to left and right human eyes; a side of each of the first cover and the second cover facing the human eye is provided with a first cavity and a second cavity in order; the first cavity is provided therein with an infrared emission module; and the second cavity is provided therein with a photo-biological training room in close contact with the human eye;

the infrared emission module includes a rubber-iron element; the rubber-iron element includes an assembly groove; the assembly groove is provided therein with a reflective film, a light guide plate, a diffusive film, a lower brightness enhancement film, an upper brightness enhancement film, and a black-black double-sided tape in order from bottom to top; the black-black double-sided tape is bonded to an inner side of the first cover or the second cover; an infrared light-emitting diode (LED) point light source is located at one side of the light guide plate and between the reflective film and the diffusive film; and the infrared LED point light source is configured to emit 600-750 nm infrared light; and the device body is provided therein with a controller; and the controller is electrically connected with the infrared LED point light source.

In a possible design, the device body is further provided therein with a music playback module; and the music playback module is electrically connected with the controller.

In a possible design, the infrared LED point light source includes a substrate layer; the substrate layer is provided thereon with a Bragg optical reflection layer; the Bragg optical reflection layer is provided thereon with an N-type aluminum gallium indium phosphide (N-AlGaInP) confinement layer with a thickness of 1,800-2,200 nm; the N-AlGaInP confinement layer is provided thereon with an I-AlGaInP active layer with a thickness of 0.1-0.3 μm; the I-AlGaInP active layer is provided thereon with a P-AlGaInP confinement layer with a thickness of 34,000-36,000 nm; and the P-AlGaInP confinement layer is provided thereon with a p-type gallium phosphide (P-GaP) window layer with a thickness of 47,000-49,000 nm; and the substrate layer includes a gallium arsenide (GaAs) substrate with a thickness of 220-320 nm; a surface of the GaAs substrate is provided with a silicon dioxide ($SiO_2$) protective layer with a thickness of 200-220 nm; a surface of the $SiO_2$ protective layer is provided with an indium tin oxide (ITO) enhancement layer with a thickness of 200-250 nm; preferably, the surface of the GaAs substrate is provided with the $SiO_2$ protective layer by a method including but not limited to electroplating; and the surface of the $SiO_2$ protective layer is provided with the ITO enhancement layer by a method including but not limited to electroplating.

In a possible design, the light guide plate is made of polymethyl methacrylate (PMMA) by laser engraving.

In a possible design, the controller includes a light emission control circuit; the light emission control circuit includes a microprocessor chip U4, which is a DC/DC step-up converter; a pin LX of the microprocessor chip U4 is connected with one terminal of an inductor L1 and a positive terminal of the infrared LED point light source; a negative terminal of the infrared LED point light source is connected with a first capacitor C3 and then grounded; a ground pin GND of the microprocessor chip U4 is grounded; a pin FB of the microprocessor chip U4 is connected with one terminal of a first resistor R13, one terminal of a second resistor R12, and a positive pole of a power supply; the other terminal of the first resistor R13 and the other terminal of the second resistor are grounded; a pin IN of the microprocessor chip U4 is connected with the other terminal of the inductor L1, one terminal of a second capacitor C2, and a 3.3 V voltage; the other terminal of the second capacitor C2 is grounded; a pin OVP of the microprocessor chip U4 is connected in series with a third resistor R9 and then connected with one terminal of the first capacitor C3 and a negative pole of the power supply; and pins EN/PWM of the microprocessor chip U4 are connected in series with a fourth resistor R10 and then connected with a power supply voltage VCC.

In a possible design, the infrared LED point light source has an emission angle of no less than 120°; and the lower brightness enhancement film and the upper brightness enhancement film each are provided with a prism with an adjustable installation angle.

In a possible design, the infrared emission module has a total thickness of no more than 0.95 mm.

In a possible design, the light guide plate has a uniformity of no less than 90%.

A second aspect of the present disclosure provides an eye training method using the intelligent photo-biological treatment device for eyes in any one of the second to seventh possible designs in the first aspect, including:

wearing and positioning the intelligent photo-biological treatment device for eyes in front of human eyes; and controlling, by the controller, the infrared emission module to emit 600-750 nm infrared light perpendicular to the human eyes, and controlling the infrared light to stimulate cone and rod cells in retinas of the human eyes for a first preset duration; and allowing the human eyes to face the photo-biological training room for an eye muscle relaxation training, and providing a voice prompt when a second preset duration is reached.

In a possible design, the method further includes:

controlling, by the controller, the music playback module to play music for a brain nerve stimulation training.

The present disclosure has the following beneficial effects:

In the present disclosure, the first cavity and the second cavity are sequentially arranged on the side of each of the first cover and the second cover of the device body facing the human eye. The first cavity is provided therein with the infrared emission module, and the second cavity is provided therein with the dark training room in close contact with the human eye. The infrared LED point light source of the infrared emission module is configured to emit 600-750 nm infrared light to stimulate the cone and rod cells in the retina of the human eye, causing the eye to secrete more dopamine. In this way, the blood vessel in the choroid of the human eye is dilated to strengthen the blood circulation in the retina and choroid, and move the thickening position of the wall of the blood vessel forward, thereby shortening the eye axis and improving uncorrected visual acuity (UCVA). The human eye observes the different colored light environments created by the photo-biological training room for a long time to relax ciliary muscles and restore their elasticity. The design improves the curvature adjustment ability of the eye lens, ensuring normal refractive adjustment of the eye. The music playback module is configured to play music, such as brainwave light music, to stimulate the brain's nervous system. The design can completely relax the brain nerves so as to relax the eye muscles of the vision system, further improving vision health.

Figure 1:
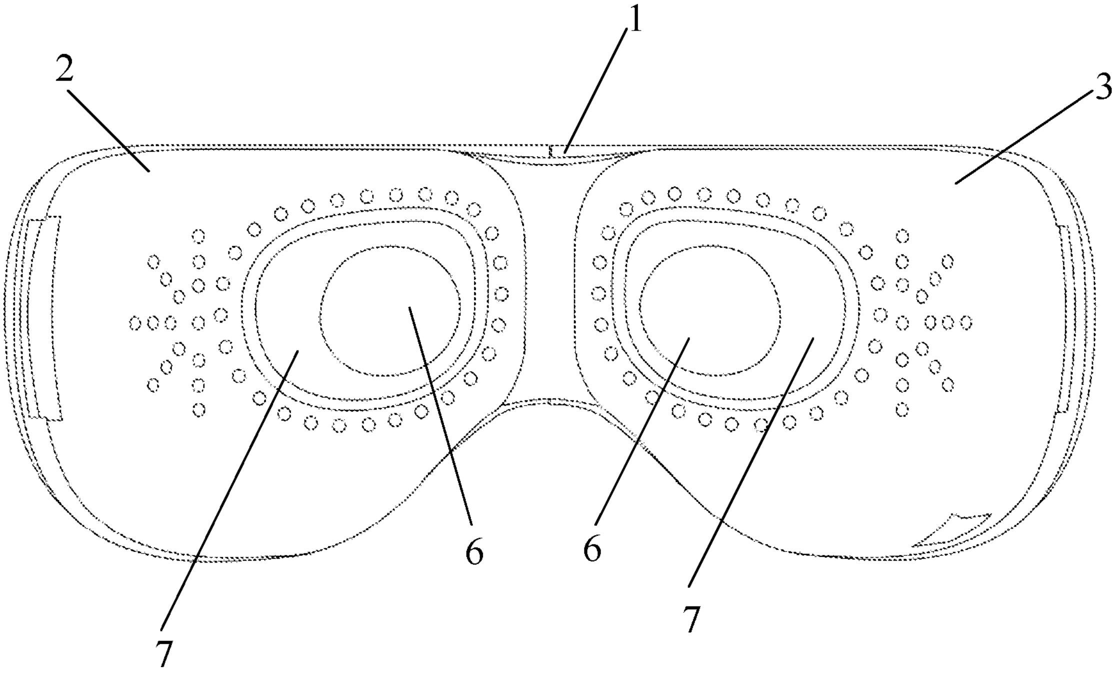
FIG. 1 is a front view of an intelligent photo-biological treatment device for eyes according to an embodiment of the present disclosure.

Reference Numerals: 1. device body; 2. first cover; 3. second cover; 4. first cavity; 5. second cavity; 6. infrared emission module; 61. rubber-iron element; 62. reflective film; 63. light guide plate; 64. diffusive film; 65. lower brightness enhancement film; 66. upper brightness enhancement film; 67. infrared light-emitting diode (LED) point light source; and 68. black-black double-sided tape.

DETAILED DESCRIPTION OF THE EMBODIMENTS

In order to make the objectives, technical solutions and advantages of the embodiments of the present disclosure clearer, the technical solutions in the embodiments of the present disclosure will be clearly and completely described below in conjunction with the drawings in the embodiments of the present disclosure. Obviously, the described embodiments are some, rather than all of the embodiments of the present disclosure. All other embodiments obtained by a person of ordinary skill in the art based on the embodiments of the present disclosure without creative efforts shall fall within the protection scope of the present disclosure.

Embodiment

Figure 2:
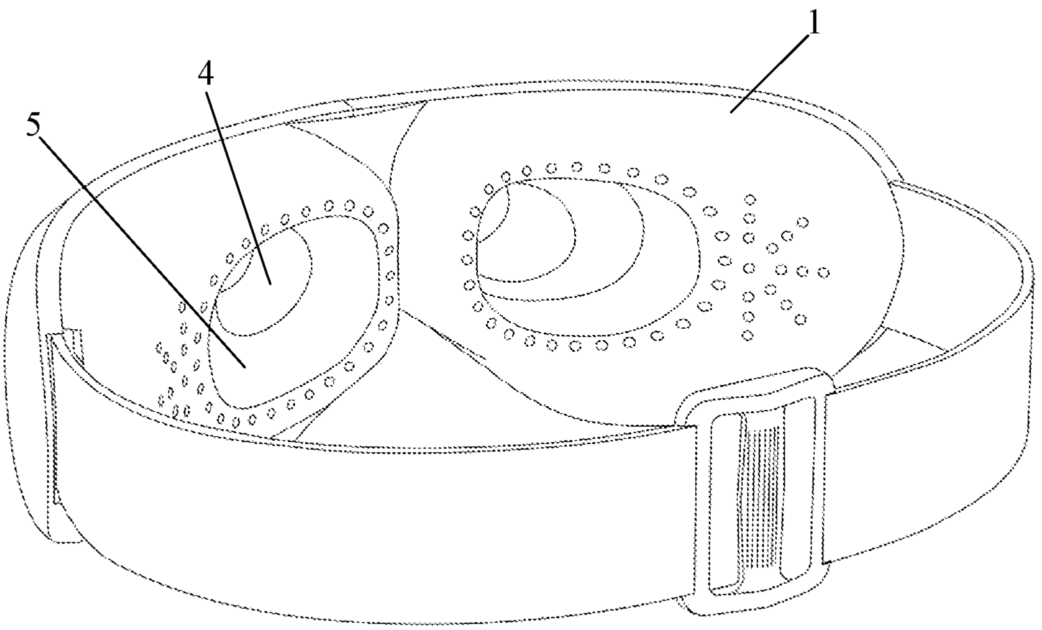
FIG. 2 is a stereoscopic view of the intelligent photo-biological treatment device for eyes according to the embodiment of the present disclosure.
Figure 3:
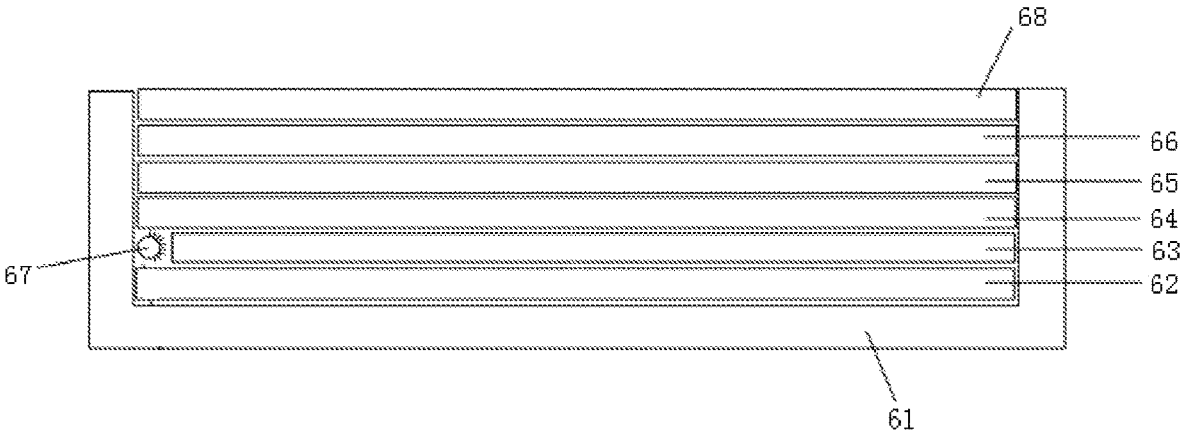
FIG. 3 is a structural view of an infrared emission module according to the embodiment of the present disclosure.
Figure 4:
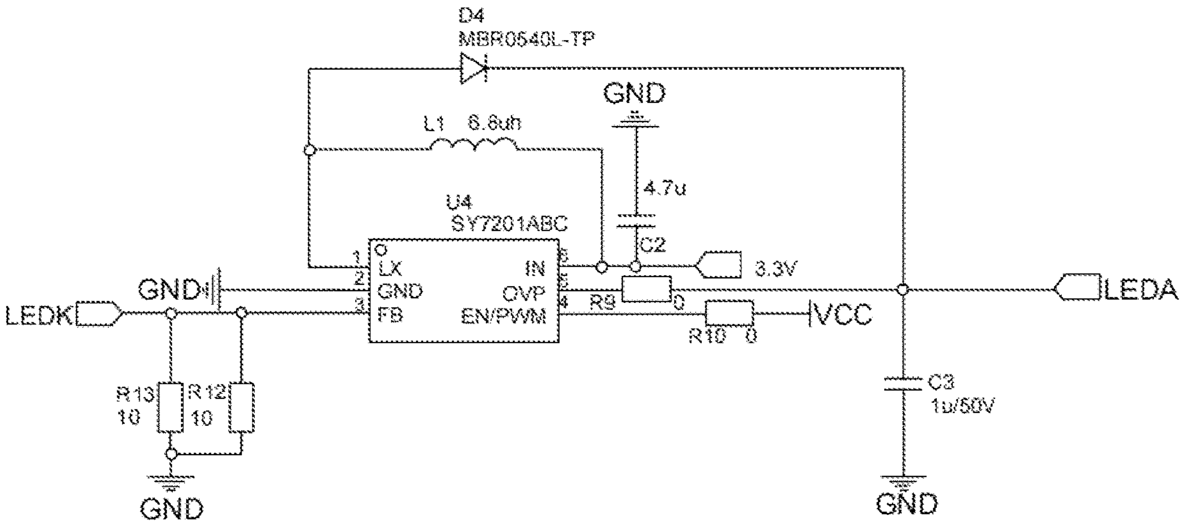
FIG. 4 is a schematic diagram of a light emission control circuit according to the embodiment of the present disclosure.

As shown in FIGS. 1 to 4, a first aspect of the present disclosure provides an intelligent photo-biological treatment device for eyes. The intelligent photo-biological treatment device for eyes includes a device body (1). The device body (1) includes a first cover (2) and a second cover (3) that are respectively adapted to left and right human eyes. A side of each of the first cover (2) and the second cover (3) facing the human eye is provided with a first cavity (4) and a second cavity (5) in order. The first cavity (4) is provided therein with an infrared emission module (6). Preferably, the infrared emission module (6) has a total thickness of no more than 0.95 mm. The second cavity (5) is provided therein with a photo-biological training room in close contact with the human eye.

The infrared emission module (6) includes a rubber-iron element (61). The rubber-iron element (61) includes an assembly groove. The assembly groove is provided therein with a reflective film (62), a light guide plate (63), a diffusive film (64), a lower brightness enhancement film (65), an upper brightness enhancement film (66), and a black-black double-sided tape (68) in order from bottom to top. The black-black double-sided tape (68) is bonded to an inner side of the first cover (2) or the second cover (3). An infrared light-emitting diode (LED) point light source (67) is located at one side of the light guide plate (63) and between the reflective film and the diffusive film (64). The infrared LED point light source (67) is configured to emit 600-750 nm infrared light.

The device body (1) is provided therein with a controller (not shown in the figure). The controller is electrically connected with the infrared LED point light source (67).

It should be noted that the assembly groove of the rubber-iron element (61) is configured to provide an assembly space for each component and plays a protective role. Preferably, the rubber-iron element (61) is integrally injection-molded. The reflective film is configured to reflect infrared light scattered from a back side of the light guide plate (63) back to the light guide plate (63), so as to increase the light brightness and uniformity. The light guide plate (63) is configured to convert the point light emitted by the infrared LED point light source (67) into an area light source, and perform transmission and heat dissipation of the light to improve the uniformity of light transmission and scattering by the light guide plate (63). Preferably, in this embodiment, the light guide plate is made of polymethyl methacrylate (PMMA, also known as acrylic or organic glass) by laser engraving, and the laser-engraved light guide plate (63) has a V-CUT pattern. The light guide plate (63) has a uniformity of no less than 90%, while the existing light guide plate (63) has a uniformity of generally not less than 80%. There are differences in the flatness and uniformity of a dot matrix pattern printed on the existing light guide plate (63) using a traditional dot printing method, and the light transmission uniformity of the existing light guide plate can only achieve ≥80%. Therefore, the light guide plate (63) in this embodiment is superior to the traditional light guide plate (63), and is effectively suitable for stimulating and training biological cells in the retina of the human eye.

It should be noted that the diffusive film (64) is configured to further improve the uniformity of the area light source through a surface diffusion particle. The lower brightness enhancement film (65) and the upper brightness enhancement film (66) are respectively configured to focus and re-diffuse the infrared light source through a surface micro-pattern, so as to further improve the brightness and uniformity of the module. The infrared LED point light source (67) has an emission angle of no less than 120°. The lower brightness enhancement film (65) and the upper brightness enhancement film (66) each are provided with a prism. The prism has an adjustable installation angle to generate focused light perpendicular to a direction of the human eye, so as to avoid overflow of the infrared light, and ultimately form infrared light perpendicular to the human eye at 90°. The design can achieve the goal of more concentrated and direct stimulation and activation of cone and rod cells in the retina of the human eye, which is beneficial for vision health. In contrast, a traditional white LED has an emission angle of not greater than 100°, such that the light emitted is scattered and cannot be focused. Therefore, this embodiment can be better used for stimulation and training of biological cells in the retina of the human eye.

Based on the disclosed content above, the first cavity (4) and the second cavity (5) are sequentially arranged on the side of each of the first cover (2) and the second cover (3) of the device body (1) facing the human eye. The first cavity (4) is provided therein with the infrared emission module (6), and the second cavity (5) is provided therein with the dark training room in close contact with the human eye. The infrared LED point light source (67) of the infrared emission module (6) is configured to emit 600-750 nm infrared light to stimulate the cone and rod cells in the retina of the human eye, causing the eye to secrete more dopamine. In this way, the blood vessel in the choroid of the human eye is dilated to strengthen the blood circulation in the retina and choroid, and move the thickening position of the wall of the blood vessel forward, thereby shortening the eye axis and improving uncorrected visual acuity (UCVA). The human eye observes the different colored light environments created by the photo-biological training room for a long time to relax ciliary muscles and restore their elasticity. The design improves the curvature adjustment ability of the eye lens, ensuring normal refractive adjustment of the eye.

In a possible design, the device body (1) is further provided therein with a music playback module (not shown in the figure). The music playback module is electrically connected with the controller. The music playback module is configured to play music, such as brainwave light music, to stimulate the brain's nervous system. The design can completely relax the brain nerves so as to relax the eye muscles of the vision system, further improving vision health.

In a possible design, the infrared LED point light source (67) includes a substrate layer. The substrate layer is provided thereon with a Bragg optical reflection layer. The Bragg optical reflection layer is provided thereon with an N-type aluminum gallium indium phosphide (N-AlGaInP) confinement layer with a thickness of 1,800-2,200 nm. The N-AlGaInP confinement layer is provided thereon with an I-AlGaInP active layer with a thickness of 0.1-0.3 μm. The I-AlGaInP active layer is provided thereon with a P-AlGaInP confinement layer with a thickness of 34,000-36,000 nm. The P-AlGaInP confinement layer is provided thereon with a p-type gallium phosphide (P-GaP) window layer with a thickness of 47,000-49,000 nm. The substrate layer includes a gallium arsenide (GaAs) substrate with a thickness of 220-320 nm. A surface of the GaAs substrate is provided with a silicon dioxide ($SiO_2$) protective layer with a thickness of 200-220 nm. A surface of the $SiO_2$ protective layer is provided with an indium tin oxide (ITO) enhancement layer with a thickness of 200-250 nm. The infrared LED point light source (67) formed by connecting these layers can emit 600-750 nm infrared light.

In a possible design, in order to control the start and stop of the infrared LED point light source, the controller includes a light emission control circuit. The light emission control circuit includes a microprocessor chip U4, which is a DC/DC step-up converter. A pin LX of the microprocessor chip U4 is connected with one terminal of an inductor L1 and a positive terminal of the infrared LED point light source. A negative terminal of the infrared LED point light source is connected with a first capacitor C3 and then grounded. A ground pin GND of the microprocessor chip U4 is grounded. A pin FB of the microprocessor chip U4 is connected with one terminal of a first resistor R13, one terminal of a second resistor R12, and a positive pole of a power supply. The other terminal of the first resistor R13 and the other terminal of the second resistor are grounded. A pin IN of the microprocessor chip U4 is connected with the other terminal of the inductor L1, one terminal of a second capacitor C2, and a 3.3 V voltage. The other terminal of the second capacitor C2 is grounded. A pin OVP of the microprocessor chip U4 is connected in series with a third resistor R9 and then connected with one terminal of the first capacitor C3 and a negative pole of the power supply. Pins EN/PWM of the microprocessor chip U4 are connected in series with fourth resistor R10 and then connected with a power supply voltage VCC.

Preferably, in this embodiment, the parameters of each circuit component of the light emission control circuit are as follows: inductance of the inductor L1: 6.8 μH (micro-henry); capacitance of the first capacitor C3: 1μ/50 V; resistance of the first resistor R13 and the second resistor R12: 10 ohms; capacitance of the second capacitor C2: 4.7μ; resistance of the third resistor R9 and the fourth resistor R10: zero. An output constant current of the light emission control circuit is OUT=200 mV, and the inductance of the inductor L1 is not greater than 6.8 μH, otherwise a power supply integrated circuit (IC) may experience severe heating.

A second aspect of the present disclosure provides an eye training method using the intelligent photo-biological treatment device for eyes in any one of the second to seventh possible designs in the first aspect, including the following steps.

The intelligent photo-biological treatment device for eyes is worn and positioned in front of human eyes. The controller controls the infrared emission module (6) to emit 600-750 nm infrared light perpendicular to the human eyes, and controls the infrared light to stimulate cone and rod cells in retinas of the human eyes for a first preset duration.

The human eyes face the photo-biological training room for an eye muscle relaxation training, and a voice prompt is provided when a second preset duration is reached.

In a possible design, the method further includes the following step.

The controller controls the music playback module to play music for a brain nerve stimulation training.

Based on the disclosed content above, in this embodiment, the infrared LED point light source (67) of the infrared emission module (6) is configured to emit 600-750 nm infrared light to stimulate the cone and rod cells in the retina of the human eye, causing the eye to secrete more dopamine. In this way, the blood vessel in the choroid of the human eye is dilated to strengthen the blood circulation in the retina and choroid, and move the thickening position of the wall of the blood vessel forward, thereby shortening the eye axis and improving uncorrected visual acuity (UCVA). The human eye observes the different colored light environments created by the photo-biological training room for a long time to relax ciliary muscles and restore their elasticity. The design improves the curvature adjustment ability of the eye lens, ensuring normal refractive adjustment of the eye. The music playback module is configured to play music, such as brainwave light music, to stimulate the brain's nervous system. The design can completely relax the brain nerves so as to relax the eye muscles of the vision system, further improving vision health.

Finally, it should be noted that the above described are only preferred embodiments of the present disclosure and are not intended to limit the present disclosure. Any modifications, equivalent substitutions, improvements, etc. made within the spirit and scope of the present disclosure should be included within the protection scope of the present disclosure.

What is claimed is:

1. An intelligent photo-biological treatment device for eyes, comprising a device body, wherein the device body comprises a first cover and a second cover that are respectively adapted to left and right human eyes; a side of each of the first cover and the second cover configured to face the corresponding one of the left and right human eyes is provided with a first cavity and a second cavity; the first cavity is provided therein with an infrared emission module; and the second cavity is provided therein with a photo-biological training part configured to be in close contact with the human eye;

the infrared emission module comprises a rubber-iron element; the rubber-iron element comprises an assembly groove; the assembly groove is provided therein with a reflective film, a light guide plate, a diffusive film, a lower brightness enhancement film, an upper brightness enhancement film, and a double-sided tape; the double-sided tape is bonded to the first cover or the second cover; an infrared light-emitting diode (LED) point light source is located at one side of the light guide plate and between the reflective film and the diffusive film; and the infrared LED point light source is configured to emit infrared light; and the device body is provided therein with a controller; and the controller is electrically connected with the infrared LED point light source;

wherein the infrared LED point light source comprises a substrate layer; the substrate layer is provided thereon with a Bragg optical reflection layer; the Bragg optical reflection layer is provided thereon with an N-type aluminum gallium indium phosphide (N-AlGaInP) confinement layer with a thickness of 1,800-2,200 nm; the N-AlGaInP confinement layer is provided thereon with an I-AlGaInP active layer with a thickness of 0.1-0.3 um; the I-AlGaInP active layer is provided thereon with a P-AlGaInP confinement layer with a thickness of 34,000-36,000 nm; and the P-AlGaInP confinement layer is provided thereon with a p-type gallium phosphide (P-GaP) window layer with a thickness of 47,000-49,000 nm; and the substrate layer comprises a gallium arsenide (GaAs) substrate with a thickness of 220-320 nm; a surface of the GaAs substrate is provided with a silicon dioxide ($SiO_2$) protective layer with a thickness of 200-220 nm; and a surface of the $SiO_2$ protective layer is provided with an indium tin oxide (ITO) enhancement layer with a thickness of 200-250 nm.

2. The intelligent photo-biological treatment device for eyes according to claim 1, wherein the device body is further provided therein with a music playback module; and the music playback module is electrically connected with the controller.

3. The intelligent photo-biological treatment device for eyes according to claim 1, wherein the light guide plate is made of polymethyl methacrylate (PMMA) by laser engraving.

4. The intelligent photo-biological treatment device for eyes according to claim 1, wherein the controller comprises a light emission control circuit; the light emission control circuit comprises a microprocessor chip, which is a DC/DC step-up converter; a switch node pin of the microprocessor chip is connected with one terminal of an inductor and a positive terminal of the infrared LED point light source; a negative terminal of the infrared LED point light source is connected with a first capacitor and then grounded; a ground pin of the microprocessor chip is grounded; a feedback pin of the microprocessor chip is connected with one terminal of a first resistor, one terminal of a second resistor, and a positive pole of a power supply; the other terminal of the first resistor and the other terminal of the second resistor are grounded; an input pin of the microprocessor chip is connected with the other terminal of the inductor L1, one terminal of a second capacitor, and a 3.3 V voltage; the other terminal of the second capacitor is grounded; an over-voltage protection pin of the microprocessor chip is connected in series with a third resistor and then connected with one terminal of the first capacitor and a negative pole of the power supply; and enable/pulse width modulation pins of the microprocessor chip are connected in series with a fourth resistor and then connected with a power supply voltage.

5. The intelligent photo-biological treatment device for eyes according to claim 1, wherein the infrared LED point light source has an emission angle of no less than 120°; and the lower brightness enhancement film and the upper brightness enhancement film each are provided with a prism with an adjustable installation angle disposed thereon.

6. The intelligent photo-biological treatment device for eyes according to claim 1, wherein the infrared emission module has a total thickness of no more than 0.95 mm.

7. The intelligent photo-biological treatment device for eyes according to claim 1, wherein the light guide plate has an optical uniformity of no less than 90%.

8. An eye training method using the intelligent photo-biological treatment device for eyes according to any one of claims 2 and 4-7, comprising:

wearing and positioning the intelligent photo-biological treatment device for eyes in front of human eyes; and controlling, by the controller, the infrared emission module to emit 600-750 nm infrared light perpendicular to the human eyes, and controlling the infrared light configured to stimulate cone and rod cells in retinas of the human eyes for a first preset duration; and positioning the photo-biological training part to face the human eyes for an eye muscle relaxation training, and providing a voice prompt when a second preset duration is reached.

9. The eye training method according to claim 8, further comprising:

controlling, by the controller, the music playback module to play music for a brain nerve stimulation training.

* * * * *